(12) United States Patent
Frensley

(10) Patent No.: US 11,234,867 B2
(45) Date of Patent: Feb. 1, 2022

(54) GOGGLE LENS CHANGING SYSTEM

(71) Applicant: Spy Optic Inc., Carlsbad, CA (US)

(72) Inventor: Christopher Frensley, Carlsbad, CA (US)

(73) Assignee: Spy Optic Inc., Carlsbad, CA (US)

( * ) Notice: Subject to any disclaimer, the term of this patent is extended or adjusted under 35 U.S.C. 154(b) by 0 days.

(21) Appl. No.: 16/042,484

(22) Filed: Jul. 23, 2018

(65) Prior Publication Data

US 2019/0038466 A1    Feb. 7, 2019

Related U.S. Application Data

(60) Provisional application No. 62/539,885, filed on Aug. 1, 2017.

(51) Int. Cl.
*A61F 9/02* (2006.01)

(52) U.S. Cl.
CPC .................... *A61F 9/025* (2013.01)

(58) Field of Classification Search
CPC ............ A61F 9/025; A61F 9/022; A61F 9/02
USPC ............ 2/429, 434, 435, 441, 443, 448, 450
See application file for complete search history.

(56) References Cited

U.S. PATENT DOCUMENTS

| | | | |
|---|---|---|---|
| 2,446,048 A | 7/1948 | Kimball |
| 2,526,737 A | 10/1950 | Farina |
| 3,056,140 A | 10/1962 | Lindholm |
| 3,298,031 A | 1/1967 | Morgan |
| 3,363,262 A | 1/1968 | Lindholm |
| 3,377,626 A | 4/1968 | Smith |
| 3,395,406 A | 8/1968 | Smith |
| 3,505,680 A | 4/1970 | Ring |
| 3,533,686 A | 10/1970 | O'Shea |

(Continued)

FOREIGN PATENT DOCUMENTS

| | | |
|---|---|---|
| CA | 2456476 | 3/2004 |
| CN | 2853028 Y | 1/2007 |

(Continued)

OTHER PUBLICATIONS

European Patent Office, Supplementary European Search Report for Application No. EP18841119, completed Mar. 22, 2021, 9 pages.

(Continued)

*Primary Examiner* — Alissa L Hoey
(74) *Attorney, Agent, or Firm* — Stetina Brunda Garred and Brucker

(57) ABSTRACT

A goggle lens is configured for use with a goggle frame having a frame body and a pair of frame engagement members positioned at respective lateral end portions of the frame body. The goggle lens includes a lens rim, and a lens element that is transparent to allow a user to view through the lens element. A pair of lens engagement members are coupled to respective lateral end portions of the lens rim. The pair of lens engagement members are selectively engageable with respective ones of the pair of frame engagement members. The pair of lens engagement members include a locking lens engagement member comprising a first element coupled to the lens rim, and a second element moveably coupled to the first element for facilitating selective engagement and disengagement with the respective one of the pair of frame engagement members.

4 Claims, 4 Drawing Sheets

(56) References Cited

U.S. PATENT DOCUMENTS

| | | |
|---|---|---|
| 3,754,298 A | 8/1973 | Menil |
| 3,783,452 A | 1/1974 | Benson et al. |
| 3,825,953 A | 7/1974 | Hunter |
| 3,896,496 A * | 7/1975 | Leblanc ............ A61F 9/025 2/439 |
| 3,924,271 A | 12/1975 | Hirschmann, Jr. |
| 3,931,646 A | 1/1976 | Loughner |
| 3,945,044 A | 3/1976 | McGee et al. |
| 4,011,595 A | 3/1977 | Shields |
| 4,149,276 A | 4/1979 | Castro |
| 4,150,443 A | 4/1979 | McNeilly |
| 4,176,410 A | 12/1979 | Matthias |
| 4,264,987 A | 5/1981 | Runckel |
| 4,290,673 A | 9/1981 | Yamamoto |
| 4,317,240 A | 3/1982 | Angerman et al. |
| 4,425,669 A | 1/1984 | Grendol et al. |
| 4,428,081 A | 1/1984 | Smith |
| 4,443,893 A | 4/1984 | Yamamoto |
| 4,447,914 A | 5/1984 | Jannard |
| 4,455,689 A | 6/1984 | Boyer |
| 4,528,701 A | 7/1985 | Smith |
| 4,556,995 A | 12/1985 | Yamamoto |
| 4,571,748 A | 2/1986 | Carroll et al. |
| 4,603,442 A | 8/1986 | Barfield |
| 4,698,838 A | 9/1987 | Angermann |
| 4,707,863 A | 11/1987 | McNeal |
| 4,716,601 A | 1/1988 | McNeal |
| 4,868,929 A | 9/1989 | Curcio |
| 4,918,753 A | 4/1990 | Mermillod |
| 4,977,627 A | 12/1990 | Metcalfe et al. |
| 4,989,274 A | 2/1991 | Patelski et al. |
| 5,018,223 A | 5/1991 | Dawson et al. |
| 5,027,443 A | 7/1991 | Watkins |
| 5,046,200 A | 9/1991 | Feder |
| 5,056,163 A | 10/1991 | Chou |
| 5,069,541 A | 12/1991 | Holmes et al. |
| 5,093,940 A | 3/1992 | Nishiyama |
| 5,138,723 A | 8/1992 | Bolle |
| 5,182,817 A | 2/1993 | Branum |
| D334,758 S | 4/1993 | Reymondet et al. |
| 5,213,241 A | 5/1993 | Dewar et al. |
| 5,216,759 A | 6/1993 | Hewitt et al. |
| 5,339,119 A | 8/1994 | Gardner |
| 5,341,516 A | 8/1994 | Keim |
| D351,850 S | 10/1994 | Bolle |
| 5,363,512 A | 11/1994 | Grabos, Jr. et al. |
| 5,371,555 A | 12/1994 | Nagel |
| 5,406,340 A | 4/1995 | Hoff |
| D358,159 S | 5/1995 | Lai |
| 5,410,763 A | 5/1995 | Bolle |
| 5,421,037 A | 6/1995 | Schulze |
| 5,423,092 A | 6/1995 | Kawai |
| 5,452,480 A | 9/1995 | Ryden |
| 5,471,036 A | 11/1995 | Sperbeck |
| D367,664 S | 3/1996 | Simioni |
| 5,495,623 A | 3/1996 | Leonardi |
| 5,517,700 A | 5/1996 | Hoffman |
| D371,566 S | 7/1996 | Kolada et al. |
| 5,542,130 A | 8/1996 | Grabos et al. |
| 5,617,588 A | 4/1997 | Canavan et al. |
| 5,628,072 A | 5/1997 | Haslbeck |
| 5,636,388 A | 6/1997 | Hodges |
| 5,642,530 A | 7/1997 | Parks |
| 5,650,866 A | 7/1997 | Haslbeck |
| 5,652,965 A | 8/1997 | Crooks |
| 5,655,228 A | 8/1997 | Chiang |
| 5,657,106 A | 8/1997 | Herald, Jr. et al. |
| 5,657,493 A | 8/1997 | Ferrero et al. |
| 5,685,022 A | 11/1997 | Essman et al. |
| 5,687,428 A | 11/1997 | Yamamoto |
| 5,689,834 A | 11/1997 | Wildon |
| 5,711,035 A | 1/1998 | Haslbeck |
| D390,248 S | 2/1998 | Pranger |
| D391,594 S | 3/1998 | Huh |
| 5,768,716 A | 6/1998 | Porsche |
| 5,802,622 A | 9/1998 | Baharad et al. |
| 5,809,580 A | 9/1998 | Arnette |
| 5,815,235 A | 9/1998 | Runckel |
| 5,818,569 A | 10/1998 | Berent |
| 5,845,341 A | 12/1998 | Barthold et al. |
| D405,102 S | 2/1999 | Moritz et al. |
| 5,867,841 A | 2/1999 | Chiang |
| D408,431 S | 4/1999 | Simioni |
| 5,915,542 A | 6/1999 | Swiet |
| 5,927,281 A | 7/1999 | Monteleone et al. |
| 5,937,439 A | 8/1999 | Barthold et al. |
| 5,940,891 A | 8/1999 | Lane |
| D413,915 S | 9/1999 | Newcomb et al. |
| 5,966,745 A | 10/1999 | Schwartz et al. |
| 5,966,746 A | 10/1999 | Reedy et al. |
| 6,009,564 A | 1/2000 | Tackles et al. |
| 6,038,707 A | 3/2000 | Ryden et al. |
| 6,047,410 A | 4/2000 | Dondero |
| 6,049,917 A | 4/2000 | Ryden |
| 6,076,196 A | 6/2000 | Masumoto |
| D428,039 S | 7/2000 | Thixton |
| 6,092,243 A | 7/2000 | Wu et al. |
| 6,094,751 A | 8/2000 | Parks |
| 6,098,204 A | 8/2000 | Arnette |
| 6,098,205 A | 8/2000 | Schwartz et al. |
| 6,099,120 A | 8/2000 | De Lima |
| 6,105,177 A | 8/2000 | Paulson et al. |
| 6,119,276 A | 9/2000 | Newcomb et al. |
| 6,138,285 A | 10/2000 | Robrahn et al. |
| 6,138,286 A | 10/2000 | Robrahn et al. |
| D439,596 S | 3/2001 | Bolle |
| D442,206 S | 5/2001 | Meyerhoffer |
| 6,227,665 B1 | 5/2001 | Pernicka et al. |
| 6,282,727 B1 | 9/2001 | Lindahl |
| 6,282,728 B1 | 9/2001 | Baragar et al. |
| D450,833 S | 11/2001 | Olivieri |
| 6,321,391 B1 | 11/2001 | Basso |
| 6,352,387 B1 | 3/2002 | Briggs et al. |
| D457,545 S | 5/2002 | Khulusi |
| D457,551 S | 5/2002 | Khulusi |
| 6,415,452 B1 | 7/2002 | Watanabe et al. |
| 6,460,196 B2 | 10/2002 | Tsubooka et al. |
| 6,467,098 B1 | 10/2002 | Lee |
| D477,010 S | 7/2003 | Moritz et al. |
| 6,611,965 B1 | 9/2003 | Lee |
| 6,611,966 B1 | 9/2003 | Yamamoto et al. |
| 6,615,409 B2 | 9/2003 | Youmans et al. |
| 6,637,038 B1 | 10/2003 | Hussey |
| 6,665,885 B2 | 12/2003 | Masumoto |
| 6,691,324 B1 | 2/2004 | Nakamura |
| 6,704,944 B2 | 3/2004 | Kawaisnshi et al. |
| 6,715,157 B2 | 4/2004 | Mage |
| 6,718,561 B2 | 4/2004 | Dondero |
| 6,728,974 B2 | 5/2004 | Wadsworth |
| 6,732,382 B2 | 5/2004 | Dondero |
| 6,732,383 B2 | 5/2004 | Cleary et al. |
| 6,772,448 B1 | 8/2004 | Hockaday et al. |
| 6,826,785 B2 | 12/2004 | McNeal |
| D505,444 S | 5/2005 | Borlet et al. |
| 6,896,366 B2 | 5/2005 | Rice et al. |
| D509,236 S | 9/2005 | Sheldon |
| 6,952,841 B2 | 10/2005 | Schary et al. |
| 6,964,067 B1 | 11/2005 | Hartman |
| 6,986,169 B2 | 1/2006 | Nakamura |
| 7,039,959 B2 | 5/2006 | Dondero |
| 7,052,127 B2 | 5/2006 | Harrison |
| 7,058,992 B1 | 6/2006 | Ogonowsky |
| 7,062,797 B2 | 6/2006 | Khulusi |
| 7,073,208 B2 | 7/2006 | Penque, Jr. et al. |
| 7,096,514 B2 | 8/2006 | Khulusi |
| 7,100,215 B2 | 9/2006 | Shiue |
| 7,137,153 B2 | 11/2006 | Hussey |
| D537,098 S | 2/2007 | Sheldon et al. |
| 7,181,779 B2 | 2/2007 | Hussey |
| 7,192,137 B2 | 3/2007 | Ishibashi et al. |
| 7,200,875 B2 | 4/2007 | Dondero |
| D542,327 S | 5/2007 | Hsu |
| D542,829 S | 5/2007 | Hsu |
| D542,830 S | 5/2007 | Hsu |

(56) References Cited

U.S. PATENT DOCUMENTS

| | | |
|---|---|---|
| 7,260,850 B2 | 8/2007 | Ambuske et al. |
| D550,749 S | 9/2007 | Chiang |
| D552,662 S | 10/2007 | Woxing |
| 7,290,294 B2 | 11/2007 | Kita |
| D559,299 S | 1/2008 | Tabacchi |
| 7,343,631 B2 | 3/2008 | Liu |
| 7,356,854 B2 | 4/2008 | Sheldon |
| 7,370,374 B2 | 5/2008 | Penque, Jr. et al. |
| 7,404,217 B2 | 7/2008 | Polinelli et al. |
| 7,407,283 B2 | 8/2008 | Babineau |
| 7,510,279 B2 | 3/2009 | Van Atta et al. |
| D591,786 S | 5/2009 | Wang |
| 7,526,813 B2 | 5/2009 | Tominaga et al. |
| D598,040 S | 8/2009 | Sheldon et al. |
| D616,915 S | 6/2010 | Silveria et al. |
| D626,166 S | 10/2010 | Yang |
| D626,582 S | 11/2010 | Cheng |
| D640,724 S | 6/2011 | Goodman et al. |
| D649,178 S | 11/2011 | Moritz et al. |
| D649,577 S | 11/2011 | Goodman et al. |
| 8,166,578 B2 | 5/2012 | Tan |
| D669,113 S | 10/2012 | Sandor et al. |
| D675,244 S | 1/2013 | Orzeck et al. |
| 8,413,267 B2 | 4/2013 | Chen |
| D685,839 S | 7/2013 | Pearson et al. |
| D687,479 S | 8/2013 | Moritz et al. |
| D687,881 S | 8/2013 | Ginther et al. |
| D688,296 S | 8/2013 | Pearson et al. |
| D695,335 S | 12/2013 | Goodman et al. |
| 8,893,314 B2 | 11/2014 | Chen et al. |
| 9,720,255 B2 | 8/2017 | Park |
| 9,895,266 B2 | 2/2018 | Reynolds et al. |
| 10,441,466 B2 * | 10/2019 | Han ................. A61F 9/025 |
| 2002/0029408 A1 * | 3/2002 | Lindahl ............. A61F 9/025 |
| | | 2/426 |
| 2002/0148034 A1 | 10/2002 | Lee |
| 2002/0157175 A1 | 10/2002 | Dondero |
| 2003/0110552 A1 | 6/2003 | Youmans et al. |
| 2005/0015862 A1 * | 1/2005 | Dondero ............ A61B 5/0002 |
| | | 2/436 |
| 2005/0128426 A1 | 6/2005 | Shiue |
| 2006/0048289 A1 | 3/2006 | Shiue |
| 2006/0176441 A1 * | 8/2006 | Katz ................... F41H 1/00 |
| | | 351/47 |
| 2006/0191062 A1 * | 8/2006 | Matera ............... A61F 9/025 |
| | | 2/426 |
| 2006/0272078 A1 | 12/2006 | Polinelli et al. |
| 2007/0033718 A1 | 2/2007 | Lin |
| 2008/0109949 A1 | 5/2008 | Kinsella |
| 2008/0155736 A1 * | 7/2008 | Paulson ............... A61F 9/025 |
| | | 2/441 |
| 2009/0019620 A1 | 1/2009 | Reed |
| 2009/0038059 A1 | 2/2009 | McNeal et al. |
| 2009/0122258 A1 | 5/2009 | Fielding, Jr. |
| 2009/0313746 A1 * | 12/2009 | Wang .................. A61F 9/025 |
| | | 2/431 |
| 2010/0064421 A1 * | 3/2010 | Wang-Lee ........... A61F 9/025 |
| | | 2/428 |
| 2010/0229292 A1 * | 9/2010 | Tan .................... A61F 9/025 |
| | | 2/452 |
| 2012/0038879 A1 | 2/2012 | Reyes et al. |
| 2014/0033408 A1 * | 2/2014 | Currens ............... A61F 9/025 |
| | | 2/431 |
| 2014/0157496 A1 * | 6/2014 | Ginther ............... A61F 9/025 |
| | | 2/439 |
| 2015/0049294 A1 * | 2/2015 | Chin ................... G02C 5/08 |
| | | 351/86 |
| 2015/0124211 A1 * | 5/2015 | Park ................... G02C 9/04 |
| | | 351/47 |
| 2015/0143619 A1 * | 5/2015 | Cross ................ A63B 33/002 |
| | | 2/427 |
| 2015/0238361 A1 * | 8/2015 | McCulloch .......... A61F 9/029 |
| | | 2/435 |
| 2018/0168865 A1 * | 6/2018 | Hilton ................ A61F 9/025 |

FOREIGN PATENT DOCUMENTS

| | | | |
|---|---|---|---|
| DE | 2063092 | 7/1971 | |
| DE | 2943472 | 5/1981 | |
| EP | 0504518 | 8/1991 | |
| EP | 1095577 | 7/2000 | |
| JP | 0956741 | 3/1997 | |
| JP | 2016131832 | 7/2016 | |
| WO | 2009101645 | 8/2009 | |
| WO | WO-2009101645 A1 * | 8/2009 | ............. A61F 9/025 |

OTHER PUBLICATIONS

National Intellectual Property Administration, PRC, Notification of the First Office Action for Application No. 201880063679.5, dated Aug. 24, 2021, 12 pages.

* cited by examiner

GOGGLE LENS CHANGING SYSTEM

CROSS-REFERENCE TO RELATED APPLICATIONS

The present application claims priority to, and the benefit of U.S. Provisional Application Ser. No. 62/539,885 entitled "GOGGLE LENS CHANGING SYSTEM" filed Aug. 1, 2017, the disclosure of which is herein incorporated by reference in its entirety.

STATEMENT RE: FEDERALLY SPONSORED RESEARCH/DEVELOPMENT

Not Applicable

BACKGROUND

1. Technical Field

The present disclosure relates generally to a goggle, and more particularly, the present disclosure relates to a goggle having a goggle lens sized and configured to be detachably connectable to a goggle frame in an easy and rapid fashion.

2. Description of the Related Art

In order to protect one's eyes during many sports or outdoor activities such as snowboarding, skiing, skydiving, paragliding, and so on, a person may wear goggles. Typically, goggles are constructed of a frame, lenses which are fixedly mounted on the forward face of the frame, padding for comfort and absorbing sweat which is attached to the rear face of the frame, and a band for fixing the goggles to a user's head. The goggles may be positioned over the user's eyes, such that the user looks through the lens, with the band extending around the user's head.

While generally all goggles share this basic design, it has been found that the experience of wearing goggles during certain sports or outdoor activities may be enhanced by wearing specialized or preferred lenses for that sport or activity. For example, variation in the colors of lenses may affect a wearer's perception of the brightness and contrast of their environment, as well as a wearer's depth perception and ability to perceive certain colors. Furthermore, the lens may be colored or have other attributes which enhance the overall aesthetic appeal of the goggle.

Lenses which are fixed to the goggle frame may limit the overall use of the goggle. For instance, the functional attributes of a given lens may be adapted for use in certain environmental conditions. For instance, darkly tinted lenses may be useful in very bright conditions, but not useful in darker conditions. Conversely, lightly tinted lenses may be useful in darker conditions, and not as useful in lighter conditions. Furthermore, the aesthetic attributes of a given lens may fall out of favor with a user as that user's aesthetic appeal changes. Additionally, during certain sports or outdoor activities, it is common that the lenses on a pair of goggles may become damaged, such as by becoming cracked, scratched, or crazed.

Thus, a wearer who owns a pair of conventional goggles with integrated lenses, but desires to wear different lenses on their goggles, or to replace damaged lenses on their goggles, may be required to purchase and adjust to an entirely new pair of goggles, or take the goggles to the manufacturer or a specialist for replacement of lenses.

Accordingly, there is a need in the art for a goggle lens which can accommodate quick and easy engagement with a corresponding goggle frame. Various aspects of the present disclosure address this particular need, as will be discussed in more detail below.

BRIEF SUMMARY

In accordance with one embodiment of the present disclosure, there is provided a goggle lens specifically sized and shaped to be detachably engageable with a frame body of the goggle. The detachable engageability of the goggle lens to the frame body allows a user to quickly and easily interchange one goggle lens with another goggle lens. As such, as environmental conditions (i.e., precipitation, light conditions, etc.) change, the user can swap out one lens, with another lens more suitable for the present conditions. The interchangability of the lens may also allow for more aesthetically appealing lenses to be used, as well as to facilitate replacement of a damaged lens with a new lens.

According to one embodiment, the goggle lens is configured for use with a goggle frame having a frame body and a pair of frame engagement members positioned at respective lateral end portions of the frame body. The goggle lens includes a lens rim, and a lens element that is transparent to allow a user to view through the lens element. A pair of lens engagement members are coupled to respective lateral end portions of the lens rim. The pair of lens engagement members are selectively engageable with respective ones of the pair of frame engagement members. The pair of lens engagement members include a locking lens engagement member comprising a first element coupled to the lens rim, and a second element moveably coupled to the first element for facilitating selective engagement and disengagement with the respective one of the pair of frame engagement members.

The first element of the lens engagement member and the lens rim may collectively define a first engagement opening, with the second element being moveable within the first engagement opening. The second element may be located within the first engagement opening to define an exposed portion of the first engagement opening. The second element may be moveable relative to the first element between a lock position and a release position, the size of the exposed portion of the first engagement opening increasing as the second element transitions from the lock position toward the release position. The goggle lens may additionally include at least one spring acting on the second element to bias the second element toward the lock position.

The second element may be moveable relative to the first element between a lock position and a release position, the second element moving away from the lens rim as the second element moves from the lock position toward the release position.

The second element may include at least one pin and the first element may include a slot adapted to receive the pin, the pin being moveable within the slot.

The lens rim may circumnavigate a lens opening, with the lens element extending across the lens opening. The lens element may include an inner lens body and an outer lens body, with the lens rim being positioned between the inner lens body and the outer lens body. The goggle lens may further comprise a gasket located between the outer lens body and the lens rim, with the gasket being sized and shaped to form a fluid-tight seal between the outer lens body and the lens rim.

At least a portion of the lens element may be tinted.

The present disclosure will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION

Figure 1:
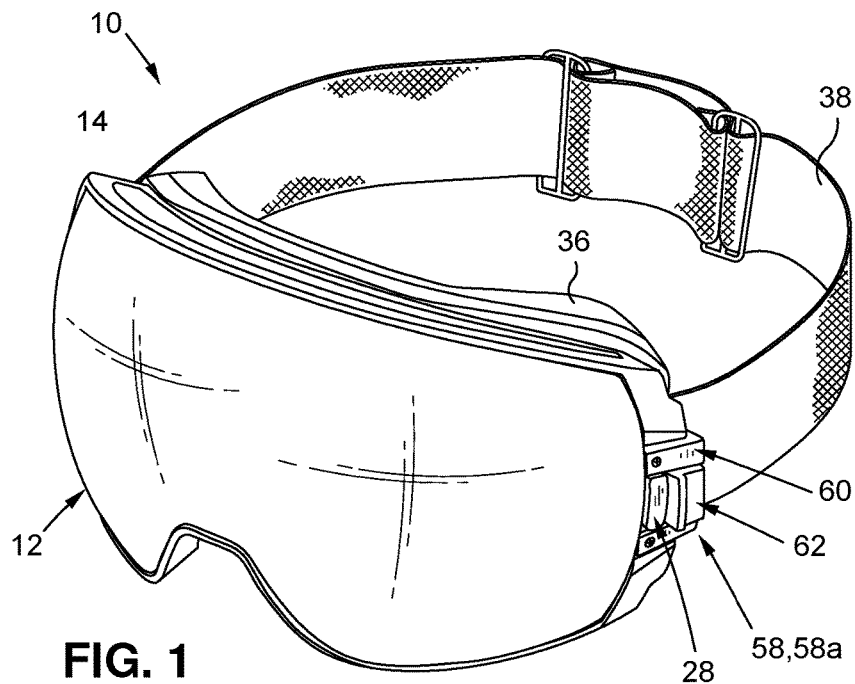
FIG. 1 is an upper perspective view of a goggle having a goggle frame and a goggle lens engaged with the goggle frame.
Figure 2:
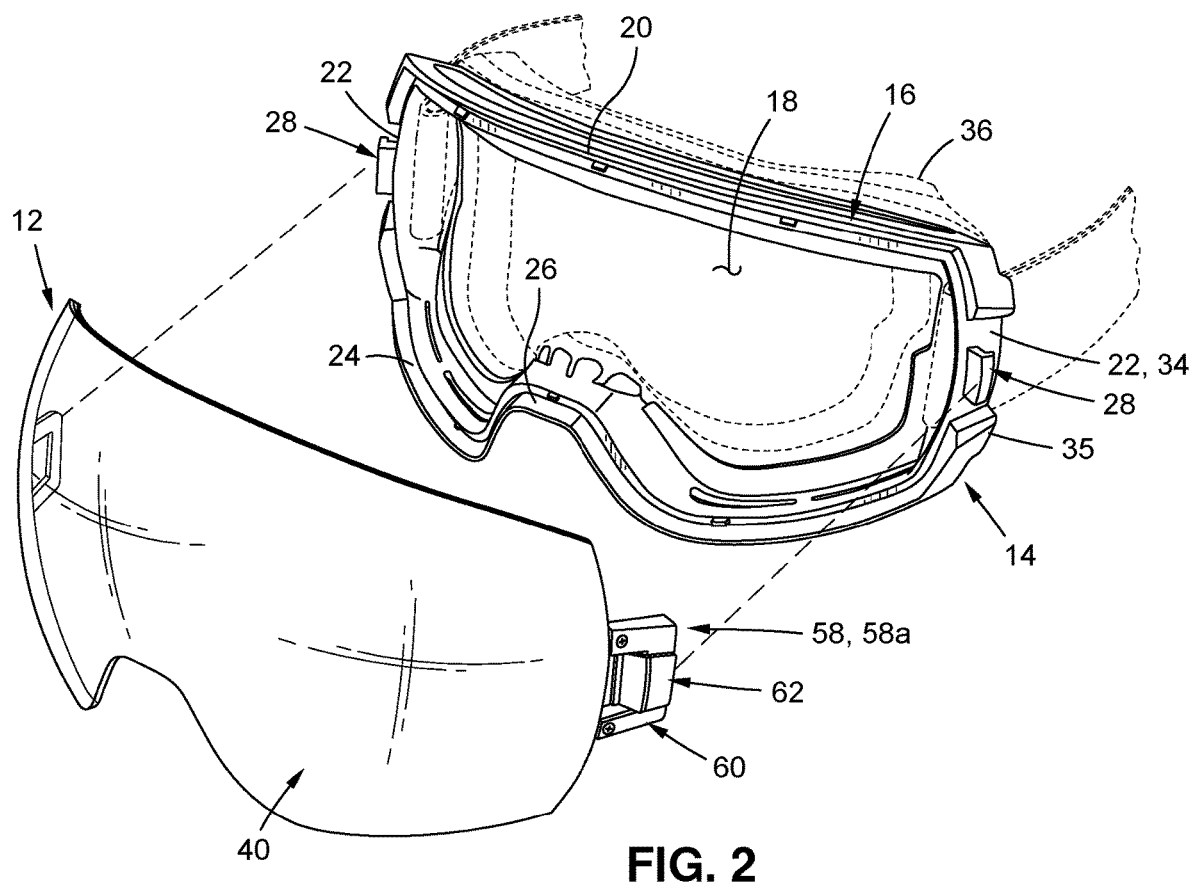
FIG. 2 is an upper perspective view of the goggle depicted in FIG. 1, with the goggle lens being detached from the goggle frame.

The detailed description set forth below in connection with the appended drawings is intended as a description of certain embodiments of a goggle lens and is not intended to represent the only forms that may be developed or utilized. The description sets forth the various structure and/or functions in connection with the illustrated embodiments, but it is to be understood, however, that the same or equivalent structure and/or functions may be accomplished by different embodiments that are also intended to be encompassed within the scope of the present disclosure. It is further understood that the use of relational terms such as first and second, and the like are used solely to distinguish one entity from another without necessarily requiring or implying any actual such relationship or order between such entities.

Referring now to the drawings, wherein the showings are for purposes of illustrating a preferred embodiment of the present disclosure, and are not for purposes of limiting the same, there is depicted a goggle 10 having a goggle lens 12 specifically configured and adapted to be detachably engageable with a goggle frame 14. The ability to quickly and easily detach the goggle lens 12 from the goggle frame 14 allows a user to utilize a goggle lens 12 that is suitable for the expected environmental conditions. For instance, a dark goggle lens may be used in bright conditions, and alternatively, a lightly tinted lens may be used in dark lighting conditions. Furthermore, one goggle lens 12 may be interchanged with another goggle lens 12 to give the overall goggle 10 a different appearance or look. As such, interchangeable goggle lenses enhance the overall commercial appeal of the goggle 10. Furthermore, interchangeable lenses allow a user to replace a broken lens 12 with a new lens 12, and thus, the user is not required to purchase an entirely new goggle 10.

According to one embodiment, the goggle frame 14 includes a frame body 16 which circumnavigates a central frame opening 18. The frame body 16 defines a curvature which allows the goggle frame 14 to comfortably fit on a user's face, with the frame body 16 including an upper portion 20 extending between a pair of lateral end portions 22, and a lower portion 24 having a centrally located bridge section 26 adapted to extend over a user's nose. The frame body 16 additionally includes a pair of frame engagement members 28 coupled to respective lateral end portions 22. In the exemplary embodiment, each frame engagement member 28 includes a finger protruding from the underlying lateral end portion 22, with the finger having a generally L-shaped configuration and including a main body 30 and a distal extension 32 extending generally perpendicularly to the main body 30. The main body 30 extends from a forward surface 34 of the lateral end portion 22. In the exemplary embodiment, the distal extension 32 on each finger extends from the main body 30 in a direction away from the central frame opening 18. The forward surface 34 from which the main body 30 extends may be recessed from a raised portion 35 of the frame body 16, with the raised portion 35 and the forward surface 34 defining a channel, the purpose of which will be described in more detail below.

At least a portion of the frame body 16 may be formed from a flexible material to enhance the fit and comfort of the goggle 10 when worn by the wearer. Exemplary flexible materials include plastic (e.g., polyurethane), rubber, or other materials known in the art.

A compressible liner 36 may extend over an inner surface of the frame body 16 (i.e., that portion of the frame body 16 facing the user during use) and may be positioned to interface with the user when the goggle 10 is worn. The compressible liner 36 may be formed from foam or other materials known in the art, and may be sized and positioned to form a barrier between the frame body 16 and the user to prevent precipitation, ice, mud, or other debris from entering the space between the goggle 10 and the user. An elastic strap 38 may be connected to the frame body 16 at the lateral end portions 22 thereof, with the strap 38 being adapted to extend around the user's head for securing the goggle 10 to the user.

Figure 3:
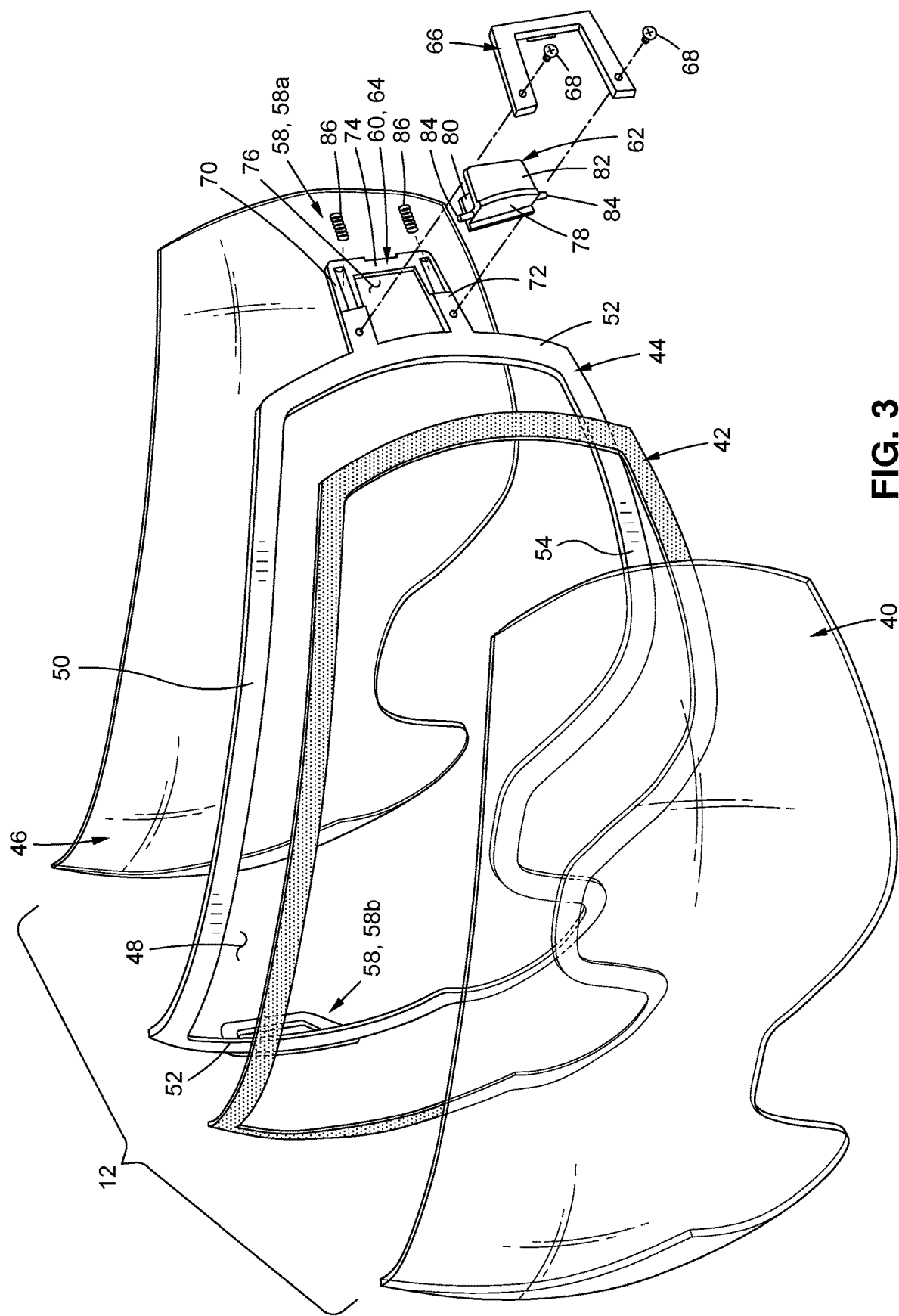
FIG. 3 is an exploded, upper perspective view of the goggle lens.

Referring now to FIG. 3, the goggle lens 12 generally includes an outer lens element 40, a lens gasket 42, a lens rim 44 and an inner lens element 46. According to one embodiment, the lens rim 44 defines a lens opening 48, with the lens rim 44 circumnavigating the lens opening 48. The lens opening 48 is substantially similar in size and shape to the central frame opening 18 defined by the frame body 16, such that when the goggle lens 12 is attached to the frame body 16, the lens opening 48 is aligned with the central frame opening 18 to allow the user to look through the goggle 10. The lens rim 44 includes an upper rim portion 50, a pair of lateral end portions 52, and a lower rim portion 54 having a bridge section shaped to extend over a user's nose during use. The lens rim 44 provides a structure upon which the outer lens element 40 and inner lens element 46 may be secured, as well as providing structure for engaging with the goggle frame 14, as will be described in more detail below.

The lens gasket 42 is adhered, or otherwise secured, to the lens rim 44. According to one embodiment, a portion of the lens gasket 42 extends from the lens rim 44 toward the center of the lens opening 48. In this regard, the inner periphery of the lens gasket 42 is spaced radially inward from the inner periphery of the lens rim 44, thus resulting in an overhanging portion of the lens gasket 42 relative to the lens rim 44. The overhanging portion is sized and shaped to interface with the inner lens element 46, as will be described in more detail below. The lens gasket 42 is formed from rubber or similar materials known in the art.

According to one embodiment, the outer lens element 40 and inner lens element 46 are coupled to opposing surfaces of the lens gasket 42, such that the lens gasket 42 resides between the outer lens element 40 and the inner lens element 46. The outer lens element 40 and inner lens element 46 are coupled to the lens gasket 42 to create a fluid tight seal with the lens gasket 42, which in turn creates a fluid-tight pocket 56 between the inner lens element 46 and the outer lens element 40. The pocket 56 helps to prevent fogging of the lens 12.

The outer lens element 40 is spaced from the lens rim 44 and extends over an outer surface of the lens rim 44 and the lens opening 48. The inner lens element 46 resides within the lens opening 48 and is sized and shaped to form an extension of the lens rim 44. The outer lens element 40 and inner lens element 46 mimic the curvature of the lens rim 44, so as to be complimentary to the lens rim 44. The outer lens element 40 is larger than the inner lens element 46, with the outer lens element 40 being sized and shaped to at least partially overlap with the lens rim 44. The inner lens element 46 is substantially the same size and shape as the lens opening 48. In this regard, the dimensioning of the inner lens element 46 and the lens rim 44 may allow the inner lens element 46 to reside within the lens opening 48.

Both the outer lens element 40 and inner lens element 46 are transparent bodies adapted to allow the user to view therethrough. As used herein, the term "transparent" simply refers to the ability of a user to at least partially look through the lens elements 40, 46. In this regard, it is understood that although the outer lens element 40 and inner lens element 46 are transparent, one or both of the outer lens element and the inner lens element 46 may have tint, polarization, film, or other aesthetic enhancements (e.g., color, reflectance, etc.) or functional enhancements (e.g., reducing glare) made thereto. The tint, polarization, or color enhancements may be functional in nature, such as reducing glare or brightness, or may be intended to enhance the overall aesthetic appeal of the goggle 10. The outer lens element 40 and inner lens element 46 may be formed of polycarbonate, TRIVEX, or other lens materials known in the art.

Although the exemplary embodiment shows the goggle lens 12 as having the outer lens element 40 and the separate inner lens element 46, it is understood that other embodiments may only include a single lens element, such as the outer lens element 40.

According to one aspect of the present disclosure, the goggle lens 12 is sized and shaped to allow for quick and easy selective detachable engagement with the goggle frame 14. The exemplary embodiment of the goggle lens 12 includes a pair of lens engagement members 58, which are selectively engageable with respective ones of the pair of frame engagement members 28. The lens engagement members 58 are coupled to respective lateral end portions 52 of the lens rim 44.

In the exemplary embodiment depicted in the drawings, the pair of lens engagement members 58 include a locking lens engagement member 58a and a fixed lens engagement member 58b. The locking lens engagement member 58a is dynamic in the sense that it is transitional between a locking configuration and a release configuration, whereas the fixed lens engagement member 58b is static, and is not transitional.

According to one embodiment, the locking lens engagement member 58a includes a first element 60 and a second element 62. The first element 60 includes a first piece 64 that is an integral extension of the lens rim 44, and a second piece 66 connectable to the first piece 64. A pair of screws 68 are used to connect the first piece 64 to the second piece 66. The first piece 64 includes an upper arm 70 and a lower arm 72, both of which extend from the lens rim 44 in generally parallel, spaced relation to each other, and a distal arm 74 extending between the upper arm 70 and the lower arm 72. The first element 60 and the lens rim 44 collectively define a first engagement opening 76.

The second element 62 includes a press plate 78, two opposing guide plates 80, 82 coupled to the press plate 78, and two spring arms 84 extending on opposed sides of the press plate 78. The second element 62 resides within the first engagement opening 76, with that portion of the first engagement opening 76 not covered by the second element 62 being an exposed portion 77 of the first engagement opening 76. A pair of springs 86 extend between the first element 60 and the second element 62 to provide a biasing force on the second element 62.

The second element 62 is moveably coupled to the first element 60 for facilitating selective engagement and disengagement with the respective one of the pair of frame engagement members 28. The second element 62 is moveable within the first engagement opening 76 relative to the first element 60 between a lock position and a release position, with the size of the exposed portion 77 of the first engagement opening 76 increasing as the second element 62 transitions from the lock position toward the release position. Conversely, as the second element 62 moves from the release position toward the lock position, the size of the exposed portion 77 of the first engagement opening 76 decreases. In the configuration shown in the drawings, the second element 62 moves away from the lens rim 44 as the second element 62 moves from the lock position toward the release position.

The fixed lens engagement member 58b extends from the lens rim 44 to define a fixed lens opening 88 which can accommodate the corresponding frame engagement member 28.

Figure 4:
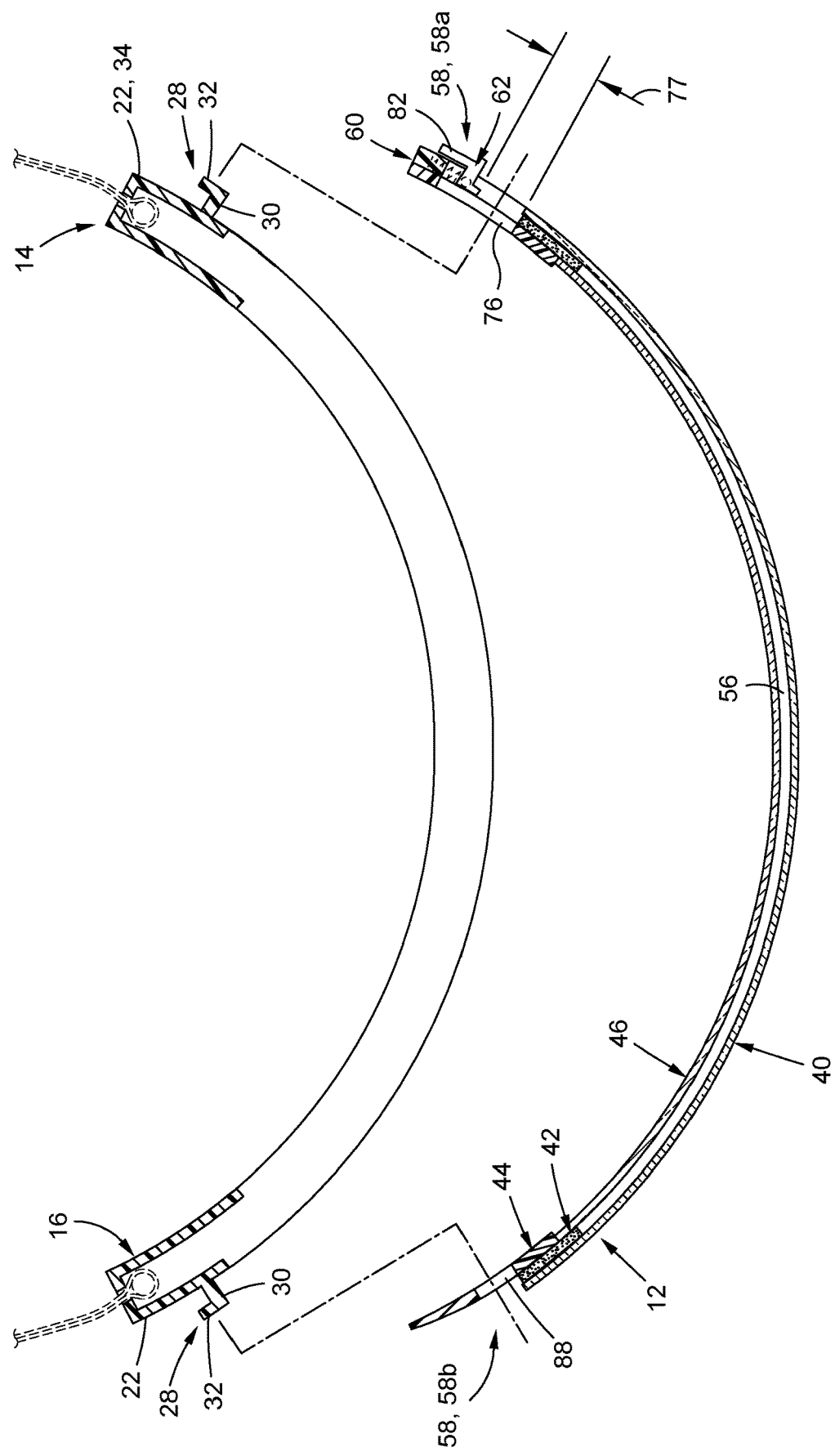
FIG. 4 is a sectional, top view of the goggle, with the goggle lens being detached from the goggle frame.
Figure 5:
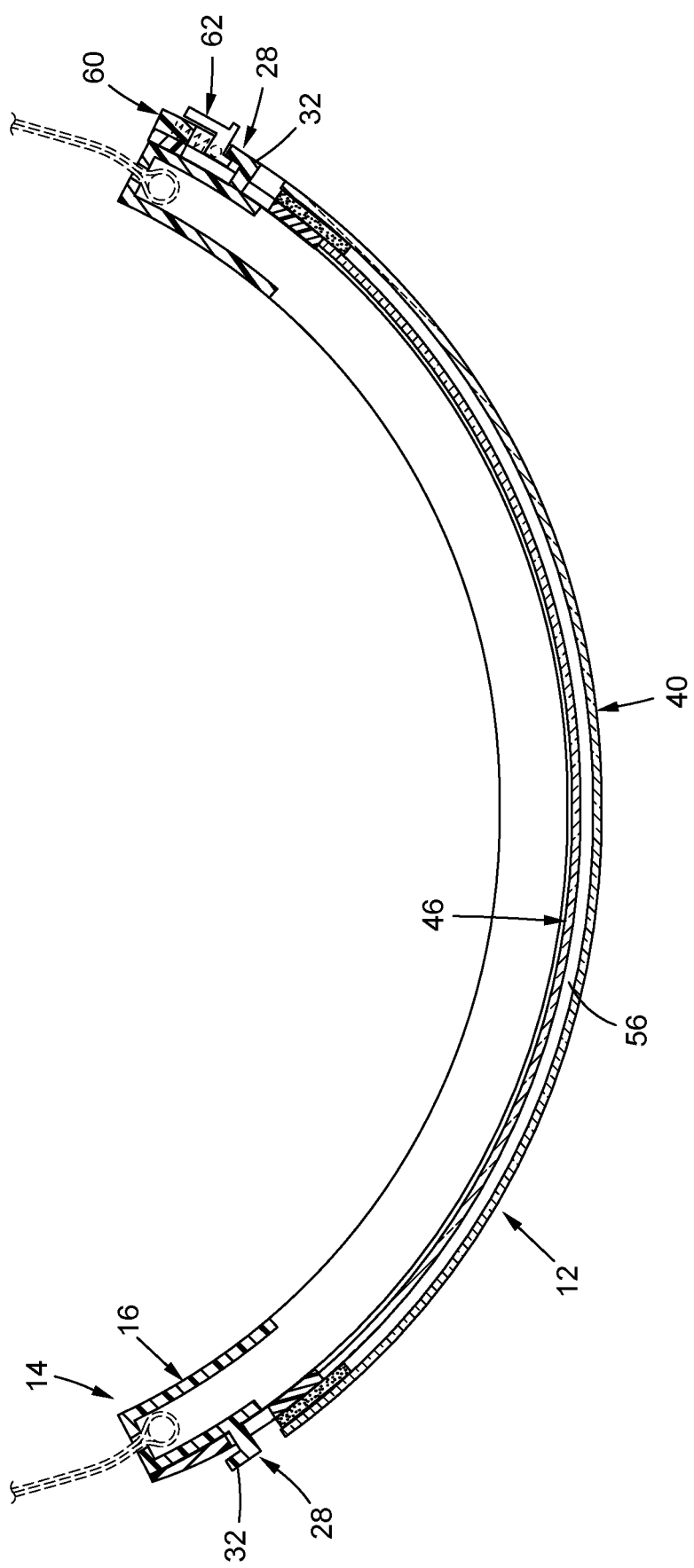
FIG. 5 is a sectional, top view of the goggle, with the goggle lens being engaged with the goggle frame.

With the basic structural features of the goggle 10 described above, a discussion of an exemplary use of the goggle 10 will now be provided. A user may have several goggle lenses 12 available for use with a goggle frame 14. When a user selects a particular goggle lens 12, the user aligns the goggle lens 12 with the goggle frame 14, as shown in FIG. 4. In particular, the goggle lens 12 is positioned with the inner lens element 46 facing toward the goggle frame 14, and the outer lens element 40 facing away from the goggle frame 14. Furthermore, the lens engagement members 58 are positioned adjacent the corresponding frame engagement members 28. The fixed lens engagement member 58b is then hooked around the corresponding frame engagement member 28. In particular, the main body 30 of the frame engagement member 28 extends through the fixed lens opening 88 and a portion of the fixed lens engagement member 58b resides between the distal extension 32 of the frame engagement member 28 and the lateral end portion 22 of the goggle frame 14.

With the fixed lens engagement member 58b connected to its corresponding frame engagement member 28, the goggle lens 12 is pivoted toward the goggle frame 14, such that the locking lens engagement member 58a moves toward its corresponding frame engagement member 28. In order to engage the locking lens engagement member 58a with its corresponding frame engagement member 28, the second element 62 is transitioned from the lock position to the release position, which enlarges the exposed portion of the first engagement opening 76. With the second element 62 in the release position, the frame engagement member 28 is advanced through the first engagement opening 76. While the main body 30 of the frame engagement member 28 resides in the first engagement opening 76, the second element 62 is transitioned from the release position to the lock position. When the second element 62 is in the lock position, the second element 62 is biased against the frame engagement member 28, which locks the goggle lens 12 to the goggle frame 14. In particular, a portion of the second element 62 of the locking lens engagement member 58b is located between the distal extension 32 of the frame engagement member 28 and the lateral end portion 22 of the goggle frame 14. When the goggle lens 12 is connected to the goggle frame 14, at least a portion of the lens engagement members 58 reside within the lateral channels 34 formed on opposite ends of the goggle frame 14.

To release the goggle lens 12 from the goggle frame 14, the second element 62 is transitioned from the lock position toward the release position to allow the frame engagement member 28 to be withdrawn from the first engagement opening 76. Once the frame engagement member 28 is removed from the first engagement opening 76, the goggle lens 12 is pivoted, such that the locking lens engagement member 58a is pivoted away from the goggle frame 14. The fixed lens engagement member 58b is then unhooked from its corresponding frame engagement member 28 to detach the goggle lens 12 from the goggle frame 14.

The incorporation of the locking lens engagement member 58a into the goggle lens 12 allows for a user to quickly and easily swap one goggle lens 12 for another goggle lens 12. The lenses may be swapped for functional reasons, such as to attach a lens having a preferred tint, or replace a broken lens; or the lenses may be swapped for aesthetic reasons. As such, the ability to easily interchange one lens for another results in a highly versatile goggle 10.

The particulars shown herein are by way of example only for purposes of illustrative discussion, and are not presented in the cause of providing what is believed to be most useful and readily understood description of the principles and conceptual aspects of the various embodiments of the present disclosure. In this regard, no attempt is made to show any more detail than is necessary for a fundamental understanding of the different features of the various embodiments, the description taken with the drawings making apparent to those skilled in the art how these may be implemented in practice.

What is claimed is:

1. A goggle lens for use with a goggle frame having a frame body and a pair of frame engagement members positioned at respective lateral end portions of the frame body, the goggle lens comprising:
   a lens rim circumnavigating a lens opening;
   a lens element secured to the lens rim so as to extend across the lens opening, the lens element defining an outer periphery and being transparent to allow a user to view through the lens element; and
   a pair of lens engagement members coupled to respective lateral end portions of the lens rim, the pair of lens engagement members being selectively engageable with respective ones of the pair of frame engagement members to selectively attach the lens rim to the goggle frame, at least one of the pair of lens engagement members including a first element coupled to the lens rim, and a second element moveably coupled to the first element for facilitating selective engagement and disengagement with the respective one of the pair of frame engagement members, a first engagement opening being defined by the first element and the lens rim and being positioned laterally outward of the outer periphery of the lens element, the second element being moveable within the first engagement opening, the second element being located within the first engagement opening to define an exposed portion of the first engagement opening, the second element being moveable relative to the first element between a lock position and a release position, a size of the exposed portion of the first engagement opening increasing as the second element transitions from the lock position toward the release position, both the first and second elements being configured to remain coupled to the lens rim when the pair of lens engagement members are disengaged from the pair of frame engagement members;
   wherein the first element includes a first arm, a second arm, and a third arm, the first and second arms extending from the lens rim in spaced relation to each other, and the third arm extending between the first and second arms;
   wherein the second element includes a first plate, a second plate, and a third plate, the second and third plates extending from the first plate in spaced relation to each other.

2. The goggle lens recited in claim 1, wherein the first plate is sized so as to fit between the first arm and the second arm of the first element.

3. A goggle comprising:
   a goggle frame having a frame body and a pair of frame engagement members, the frame body having a rearward portion configured to face a user when worn by the user, and a forward portion opposite the rearward portion, the frame engagement members projecting forwardly from the frame body and positioned at respective lateral end portions of the frame body; and
   a goggle lens selectively engageable with the goggle frame, the goggle lens comprising:
      a lens rim circumnavigating a lens opening;
      a lens element secured to the lens rim so as to extend across the lens opening, the lens element being transparent to allow a user to view through the lens element; and
      a pair of lens engagement members coupled to respective lateral end portions of the lens rim, the pair of lens engagement members being selectively engageable with respective ones of the pair of frame engagement members to selectively attach the lens rim to the goggle frame, the pair of lens engagement members including a locking lens engagement member removable from the frame and comprising a first element coupled to the lens rim, and a second element moveably coupled to the first element for facilitating selective engagement and disengagement with the respective one of the pair of frame engagement members, a first engagement opening being defined by the first element and the lens rim, the second element being moveable within the first engagement opening, the second element being located within the first engagement opening to define an exposed portion of the first engagement opening, the second element being moveable relative to the first element between a lock position and a release position, a size of the exposed portion of the first engagement opening increasing as the second element transitions from the lock position toward the release position, both the first and second elements being configured to remain coupled to the lens rim when the pair of lens engagement members are disengaged from the pair of frame engagement members;
   wherein the first element includes a first arm, a second arm, and a third arm, the first and second arms extending from the lens rim in spaced relation to each other, and the third arm extending between the first and second arms;
wherein the second element includes a first plate, a second plate, and a third plate, the second and third plates extending from the first plate in spaced relation to each other.

4. A goggle lens for use with a goggle frame having a frame body and a pair of frame engagement members positioned at respective lateral end portions of the frame body, the goggle lens comprising:
a lens rim circumnavigating a lens opening;
a lens element secured to the lens rim so as to extend across the lens opening, the lens element being transparent to allow a user to view through the lens element; and
a pair of lens engagement members coupled to respective lateral end portions of the lens rim, the pair of lens engagement members being selectively engageable with respective ones of the pair of frame engagement members to selectively attach the lens rim to the goggle frame, at least one of the pair of lens engagement members including a first element coupled to the lens rim, and a second element moveably coupled to the first element for facilitating selective engagement and disengagement with the respective one of the pair of frame engagement members, a first engagement opening being defined by the first element and the lens rim and being positioned laterally outward of the outer periphery of the lens element, the second element being moveable within the first engagement opening, the second element being located within the first engagement opening to define an exposed portion of the first engagement opening, the second element being moveable relative to the first element between a lock position and a release position, a size of the exposed portion of the first engagement opening increasing as the second element transitions from the lock position toward the release position, both the first and second elements being configured to remain coupled to the lens rim when the pair of lens engagement members are disengaged from the pair of frame engagement members;
wherein the first element includes a first arm, a second arm, and a third arm, the first and second arms extending from the lens rim in spaced relation to each other, and the third arm extending between the first and second arms, and the second element includes a first plate, a second plate, and a third plate, the second and third plates extending from the first plate in spaced relation to each other.

* * * * *